United States Patent [19]

Green

[11] Patent Number: 5,423,856
[45] Date of Patent: Jun. 13, 1995

[54] APPARATUS AND METHOD FOR SUBCUTICULAR STAPLING OF BODY TISSUE

[75] Inventor: David T. Green, Westport, Conn.

[73] Assignee: United States Surgical Corporation, Norwalk, Conn.

[21] Appl. No.: 101,656

[22] Filed: Aug. 4, 1993

Related U.S. Application Data

[63] Continuation of Ser. No. 581,776, Sep. 13, 1990, abandoned.

[51] Int. Cl.$^6$ ............................................. A61B 17/04
[52] U.S. Cl. ..................................... 606/215; 606/219; 227/175
[58] Field of Search ............... 606/142, 144, 151, 213, 606/219, 221, 218, 215; 411/451, 452, 455, 487, 489, 495, 411, 424; 224/175, 176; 227/175

[56] References Cited

U.S. PATENT DOCUMENTS

| | | | |
|---|---|---|---|
| 2,182 | 7/1841 | Ballard . | |
| 415,175 | 11/1889 | Prouty . | |
| 715,612 | 12/1902 | Van Schott . | |
| 816,026 | 3/1906 | Meir . | |
| 1,200,594 | 10/1916 | Curtis | 411/455 |
| 1,452,373 | 4/1923 | Gomez . | |
| 1,906,527 | 5/1933 | Bradley | 411/451 |
| 1,933,317 | 10/1933 | Curtis | 411/451 |
| 2,254,620 | 9/1941 | Miller . | |
| 2,356,376 | 8/1944 | Brown, Jr. . | |
| 2,668,538 | 2/1954 | Baker . | |
| 2,811,971 | 11/1957 | Scott . | |
| 2,910,067 | 10/1959 | White . | |
| 3,003,155 | 10/1961 | Mielzunski et al. . | |
| 3,110,899 | 11/1963 | Warren | 606/139 |
| 3,150,379 | 9/1964 | Brown . | |
| 3,203,220 | 8/1965 | Kaepernik . | |
| 3,205,757 | 9/1965 | Kuennen | 411/498 |
| 3,378,010 | 4/1968 | Codling et al. . | |
| 3,618,447 | 11/1971 | Goins . | |
| 3,631,707 | 1/1972 | Miller . | |
| 3,716,058 | 2/1973 | Tanner, Jr. . | |
| 3,845,772 | 11/1974 | Smith | 128/335 |
| 4,052,988 | 10/1977 | Doddi et al. . | |
| 4,064,881 | 12/1977 | Meredith . | |
| 4,162,678 | 7/1979 | Fedotov et al. | 227/19 |
| 4,164,225 | 8/1979 | Johnson et al. | 606/144 |

(List continued on next page.)

FOREIGN PATENT DOCUMENTS

| | | |
|---|---|---|
| 256506 | 5/1963 | Australia . |
| 0173451 | 3/1986 | European Pat. Off. . |
| 0260970 | 3/1988 | European Pat. Off. . |
| 0392750 | 10/1990 | European Pat. Off. . |
| 2308349 | 11/1976 | France . |
| 2606270 | 5/1988 | France . |
| 2740274 | 3/1978 | Germany . |
| 8522122 | 10/1985 | Germany . |
| 166352 | 3/1984 | Switzerland . |
| 873960 | 8/1961 | United Kingdom . |

(List continued on next page.)

OTHER PUBLICATIONS

Russell Warren, M.D., Technique for Using the Tag Tissue Anchor—Rod Style, Published Jul. 16, 1990.
John O. Hayhurst, M.D., Technique for Using the Tag Tissue Anchor—Wedge Style, Published Jul. 16, 1990.
Arthrex Brochure—"Arthrex ESP System: Expanding (List continued on next page.)

*Primary Examiner*—Gary Jackson

[57] ABSTRACT

A surgical apparatus is disclosed for attaching adjacent end portions of cutaneous body tissue wherein a pair of opposed jaws have means for moving the jaws toward and away from each other. Body tissue engaging means in the form of sharp tip members extend from each jaw and toward the other so as to engage the opposed portions of cutaneous tissue when the jaws are positioned thereagainst and moved toward each other. The jaws and the tips are arranged to cause the cutaneous tissue to assume an irregular shape at the interface whereby an elongated member may be directed generally medially of the interface of the tissue to attach the opposed portions to thereby permit healing. A method of attaching adjacent end portions of cutaneous body tissue surrounding an opening utilizing the apparatus of the invention is also disclosed.

60 Claims, 3 Drawing Sheets

U.S. PATENT DOCUMENTS

| | | | |
|---|---|---|---|
| 4,256,251 | 3/1981 | Moshofsky | 227/120 |
| 4,345,600 | 8/1982 | Rothfuss . | |
| 4,399,810 | 8/1983 | Sanuels et al. | 227/19 |
| 4,409,974 | 10/1983 | Freedland | 128/92 |
| 4,448,194 | 5/1984 | DiGiovanni et al. . | |
| 4,454,875 | 6/1984 | Pratt et al. | 128/92 |
| 4,493,322 | 1/1985 | Becht | 227/19 |
| 4,506,669 | 3/1985 | Blake, III | 606/218 |
| 4,523,591 | 6/1985 | Kaplan et al. . | |
| 4,523,695 | 6/1985 | Braun et al. | 227/19 |
| 4,526,173 | 7/1985 | Sheehan . | |
| 4,527,725 | 7/1985 | Poslien | 227/19 |
| 4,532,926 | 8/1985 | O'Holla | 128/334 |
| 4,535,772 | 8/1985 | Sheehan . | |
| 4,595,007 | 6/1986 | Mericle . | |
| 4,605,002 | 8/1986 | Rebuffat . | |
| 4,610,251 | 9/1986 | Kumar . | |
| 4,612,923 | 9/1986 | Kronenthal . | |
| 4,653,486 | 3/1987 | Coker | 128/92 |
| 4,688,560 | 8/1987 | Schultz | 606/73 |
| 4,712,550 | 12/1987 | Sinnett . | |
| 4,744,365 | 5/1988 | Kaplan et al. . | |
| 4,753,636 | 6/1988 | Free . | |
| 4,776,328 | 10/1988 | Frey et al. | 128/92 |
| 4,815,468 | 3/1989 | Annand . | |
| 4,832,026 | 5/1989 | Jones . | |
| 4,834,098 | 5/1989 | Jones . | |
| 4,841,960 | 6/1989 | Garner . | |
| 4,858,603 | 8/1989 | Clemow et al. . | |
| 4,865,032 | 9/1989 | Jones . | |
| 4,869,242 | 9/1989 | Galluzzo . | |
| 4,873,976 | 10/1989 | Schreiber | 606/213 |
| 4,874,122 | 10/1989 | Froelich et al. . | |
| 4,887,756 | 12/1989 | Puchy | 227/19 |
| 4,895,148 | 1/1990 | Bays et al. . | |
| 4,898,186 | 2/1990 | Ikada et al. . | |
| 4,899,745 | 2/1990 | Laboureau et al. . | |
| 4,924,866 | 5/1990 | Yoon . | |
| 4,944,742 | 7/1990 | Clemow et al. . | |
| 4,946,468 | 8/1990 | Li | 606/232 |
| 4,973,211 | 11/1990 | Potucek . | |
| 4,976,686 | 12/1990 | Ball et al. | 604/61 |
| 5,002,550 | 3/1991 | Li | 606/139 |
| 5,004,469 | 4/1991 | Palmieri et al. | 606/139 |
| 5,007,921 | 4/1991 | Brown . | |
| 5,026,374 | 6/1991 | Dezza et al. | 606/73 |
| 5,037,422 | 8/1991 | Hayhurst et al. | 606/72 |
| 5,047,047 | 9/1991 | Yoon . | |
| 5,156,609 | 10/1992 | Nakao et al. . | |
| 5,158,566 | 10/1992 | Pianetti . | |

FOREIGN PATENT DOCUMENTS

| | | | |
|---|---|---|---|
| 1172775 | 12/1969 | United Kingdom | 227/175 |
| 1350100 | 4/1974 | United Kingdom | 606/138 |
| 2162782 | 2/1986 | United Kingdom . | |
| 888965 | 12/1981 | U.S.S.R. | 606/144 |
| 1210801 | 2/1986 | U.S.S.R. . | |
| 8503857 | 9/1985 | WIPO . | |
| WO89/01767 | 3/1989 | WIPO . | |
| 8901767 | 3/1989 | WIPO . | |
| WO89/10096 | 11/1989 | WIPO . | |

OTHER PUBLICATIONS

Suture Plug"—Feb., 1991? [Published prior to Mar. 1, 1991].

Peacock, Erle E., *Wound Repair*, 1984, 141–158.

"United States Surgical Corporation Information Booklet for Auto Suture ™ Purse String Instrument", copyright 1977, 1978, United States Surgical Corporation.

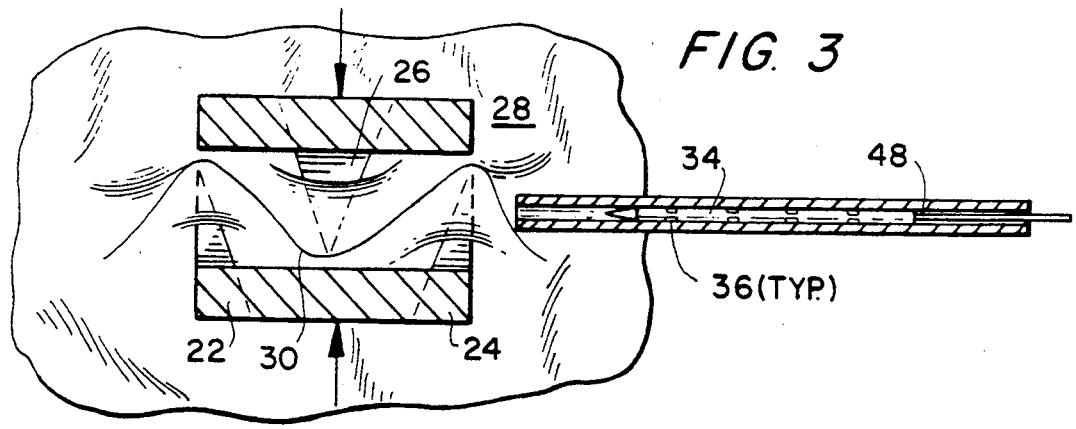
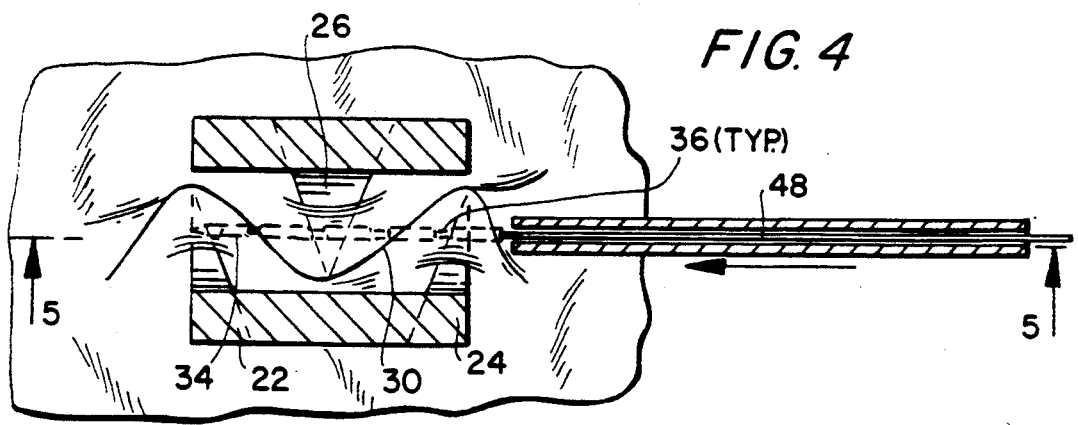
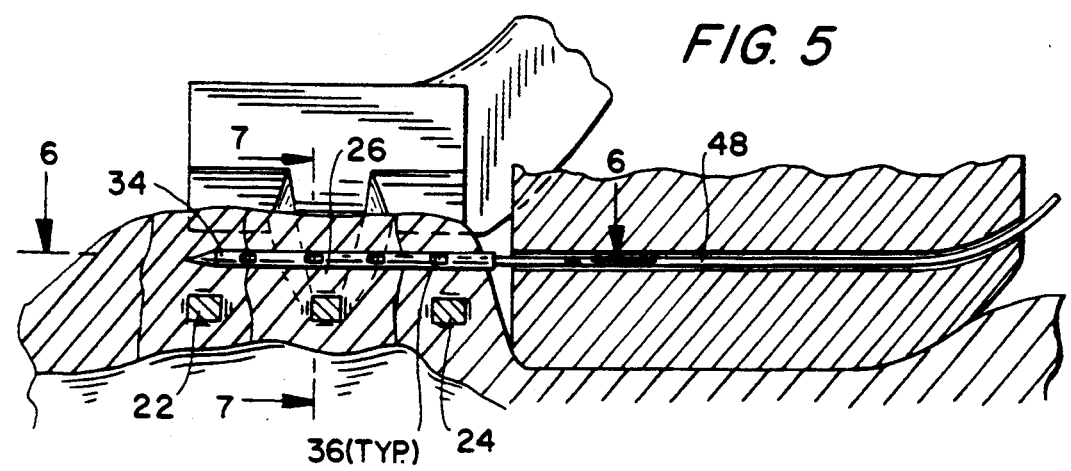

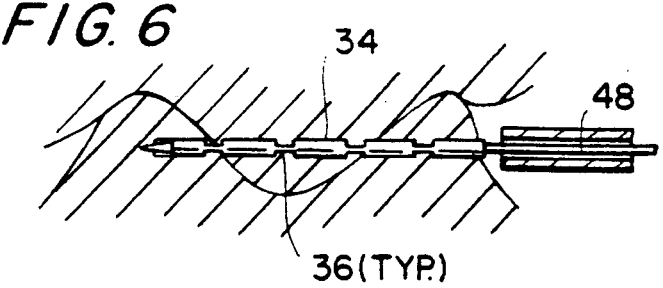
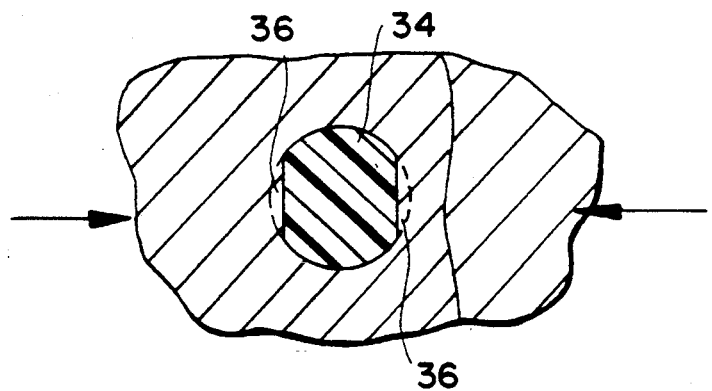
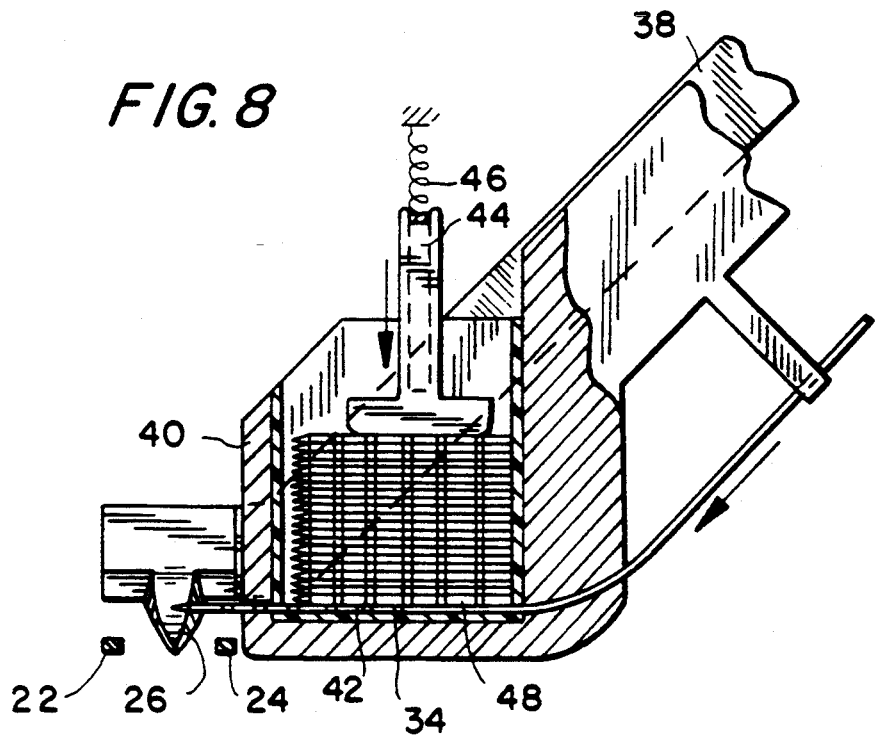

APPARATUS AND METHOD FOR SUBCUTICULAR STAPLING OF BODY TISSUE

This is a continuation of application Ser. No. 07/581,776 filed on Sep. 13, 1990, now abandoned.

BACKGROUND OF THE INVENTION

1. Field of the Invention

The present invention relates to an apparatus and method for subcuticular attachment of skin surrounding an opening wherein the opening is either caused unintentionally or by surgical procedure.

2. Description of the Prior Art

Modern day surgery using sutures and staples or the like is well defined. Generally, the key to successfully attaching cutaneous matter is the utmost gentleness in handling all tissue. Damaged and injured tissue leads to necrosis followed by fibrosis and scarring.

In handling tissue for attaching the surgical ends adjacent an opening, care must be taken in attaching the open ends to provide a minimum of the usual well-known telltale marks in the skin. For example, the application of sutures in cutaneous surgery will often result in the appearance of telltale crosshatch markings, whereas the use of sutures subcutaneously allows for early removal to minimize the telltale marks. Application of subcutaneous sutures generally refers to introduction of sutures at well below the epidermis and dermis. Subcuticular sutures generally refer to sutures introduced beneath the epidermis. In any event, reference to attachment of cutaneous matter below the epidermis at any level is sometimes referred to as "subcutaneous".

Surgically attaching cutaneous matter is also accomplished by application of staples which are generally of a metal material and are closed by action against an anvil which causes the ends of the staple to close after anvil which causes the ends of the staple to close after piercing the skin surrounding an opening. In either case, the portions of skin are first drawn together and then stapled or sutured so as to hold them together until natural healing takes place. The steps are often cumbersome to the surgeon since holding the skin together requires one motion and stapling or suturing requires another.

To date, there does not appear to exist an apparatus which is capable of gripping the portions of cutaneous matter surrounding an opening and drawing them together, followed by introduction of a staple at subcuticular levels, i.e. below the epidermis. Neither does there appear to exist an apparatus which is capable of drawing the cutaneous matter together and firing a staple in the subcutaneous region, i.e. in the region below the dermis. The present invention is directed to such an apparatus and method for attachment of cutaneous matter.

SUMMARY OF THE INVENTION

A surgical apparatus for attaching at least two adjacent end portions of a medium such as cutaneous body tissue which comprises a pair of jaws, means for moving the jaws toward and away from each other, and body tissue engaging means extending from each jaw and facing the opposed jaw and adapted to engage the respective opposed portions of the medium such that when the jaws are moved toward each other said engaging means causes the two end portions of the medium to be displaced toward each other and to assume an irregular or undulating shape whereby an elongated member may be directed generally medially of the medium to thereby attach opposed portions of the medium.

Means is provided to direct an elongated attaching member generally medially of the interface and subcuticularly of the body tissue to thereby attach the end portions. Preferably, each jaw includes a sharp pointed member positioned for engagement with marginal end portions of skin adjacent an opening therein such that when the jaws are displaced toward each other, the skin portions move toward each other and into engagement and assume an undulating configuration at the interface therebetween. The apparatus further comprises a cartridge positioned adjacent the jaws and adapted to support a plurality of elongated skin attaching members.

Each skin attaching member is preferably a rod-like member having a sharp pointed tip at the distal end to facilitate subcuticular penetration of the skin. Further, each rod-like member includes at least one slot extending at least partially around a peripheral portion thereof.

In the preferred embodiment the cartridge is adapted to contain a plurality of the rod-like members and includes means to resiliently bias the rod-like members toward a position for advancing the member distally toward the body tissue when the body tissue is gripped by the sharp pointed members. The members are of length sufficient to engage oppositely sloped skin portions as determined by the dimensions and relative spacing of the pointed tips. Further, the rod-like members include means on the outer surface to retain them in position within the body tissue.

A method is also disclosed for attaching two adjacent end portions of skin surrounding an opening comprising gripping one marginal end portion of the skin adjacent the opening at two spaced locations, gripping the opposite marginal end portion of the skin at a location generally medial of the two locations at which the first marginal end portion is gripped, displacing the two end portions of skin surrounding the opening toward each other sufficient to cause the end portions to engage each other and to assume an undulating shape, and introducing an elongated staple into the end portions of the skin subcuticularly, the elongated staple being of length sufficient to penetrate at least two spaced portions of skin on the same side of the opening so as to retain the marginal end portions together in end to end contacting relation to promote healing. Preferably, as noted, the method comprises configuring the staple to have an irregular outer surface to prevent the staple from working itself out of the subcuticular region.

Preferably, the method is practiced utilizing sharp skin engaging members attached to jaws as described to permit gripping the skin and bringing the end portions adjacent an opening to form the undulating shape.

According to the method contemplated, the staple may also be inserted subcutaneously.

BRIEF DESCRIPTION OF THE ACCOMPANYING FIGURES

Preferred embodiments of the invention are described hereinbelow with reference to the drawings herein:

FIG. 3 is a view from above, greatly enlarged and partially in cross-section, of the pointed gripping members of the apparatus of FIG. 1, just prior to subcuticular introduction of a staple;

FIG. 4 is a view from above, similar to FIG. 3 after subcuticular introduction of the staple;

FIG. 5 is a view partially in cross-section, taken along lines 5—5 of FIG. 4 and illustrating the subcuticularly positioned staple after firing the apparatus;

FIG. 6 is a view partially in cross-section, taken along lines 6—6 of FIG. 5;

FIG. 7 is a cross-sectional view, greatly enlarged, taken along lines 7—7 of FIG. 5, illustrating the staple subcuticularly embedded in the skin portions attached thereby; and FIG. 8 is a greatly enlarged side view, partially in cross-section, illustrating the staple cartridge which forms part of the invention.

DETAILED DESCRIPTION OF THE PREFERRED EMBODIMENTS

Figure 1:
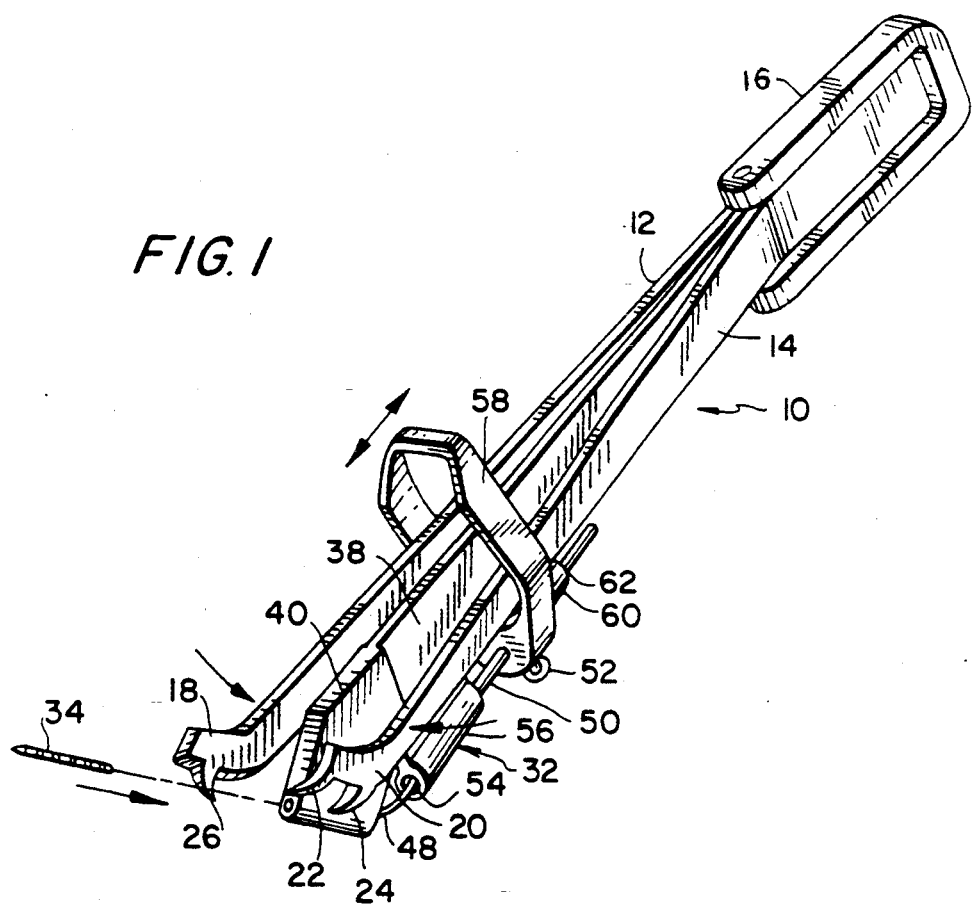
FIG. 1 is a perspective view of the apparatus for stapling body tissue according to the invention.

FIG. 1 illustrates the apparatus 10 for subcuticular stapling of skin, constructed according to the present invention. The apparatus 10 includes elongated arms 12 and 14 connected as shown by end bracket 16 and resiliently biased away from each other. The resilient outward bias may be provided naturally by fabricating the arms 12 and 14 of a resilient material such as spring steel, or optionally may be provided by incorporating a separate resilient spring in region of connecting bracket 16.

The lower end portion of each arm is constructed as shown. Arm 12 includes an extension or jaw 18 oriented at an appropriate obtuse angle with respect to the main portion of the arm and arm 14 includes a similar extension or jaw 20 as shown. The extension 20 includes sharp pointed skin gripping tips 22, 24 spaced apart from each other and extending generally downwardly and toward extension 18. Extension 18 includes a similarly shaped skin gripping tip 26 oriented generally downwardly and extending toward extension 20. The position of skin gripping tip 26 on extension 18 is preferably such as to be located medially between skin gripping tips 22, 24 when the arms 12 and 14 are manually brought together to grip the skin surrounding an opening as will be described. Each skin gripping tip 26, 22, 24 includes a broad base area to facilitate grasping the skin with minimum cutting after the sharp tip has penetrated the surface. Alternatively, a different number of skin gripping tips could be provided on each arm.

Figure 2:
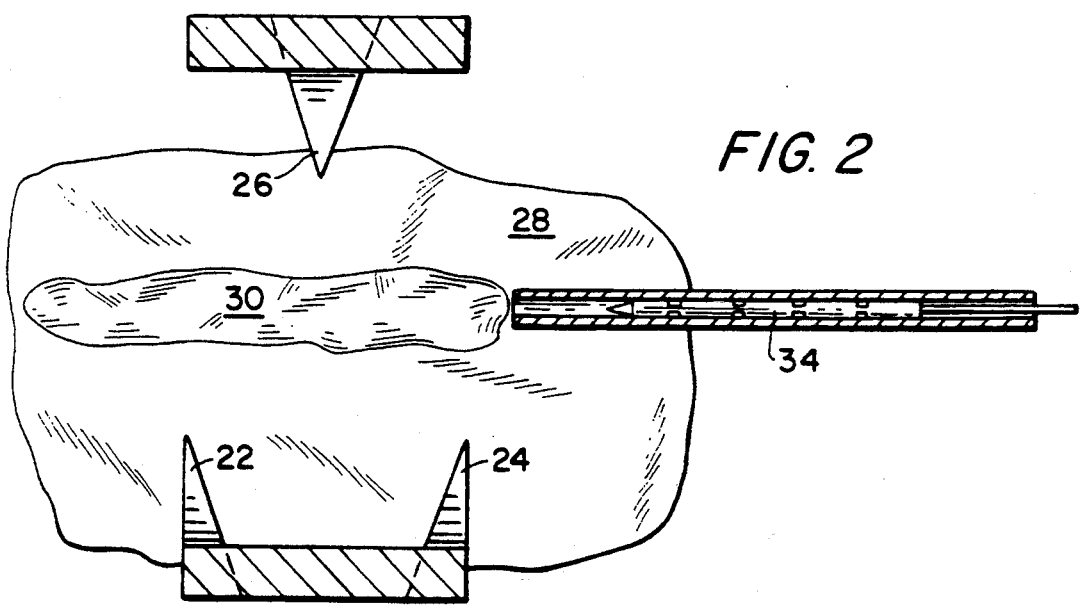
FIG. 2 is a view from above, greatly enlarged, illustrating the pointed gripping members of the apparatus of FIG. 1 prior to gripping the body tissue for subcuticular attachment.

Referring now to FIG. 2, the basic operative principles of the invention will be described. There is illustrated the upper surface of skin 28 surrounding an opening such as a wound or surgically provided opening. The apparatus is positioned such that extensions 18, 20 may be positioned in contact with, and generally parallel to the upper surface of the skin. To close the opening in the skin the extensions are advanced downwardly against the skin sufficient to cause piercing tips 22, 24 and 26 to pierce the skin minimally as shown. Thereafter, the arms 12, 14 are squeezed together by the surgeon to cause the three sharp tips to join the skin portions surrounding the opening as shown in FIG. 3, i.e. to assume an undulating, or sinusoidal shape. Then, the staple actuating mechanism 32 is fired to caused the elongated staple 34 to penetrate the tissue below the upper epidermal layer and to retain the separate portions of skin in interfacial engaged relation as shown in FIG. 4. Thus, the opening in the skin is prepared for natural permanent healing and adhesion with minimum or no scarring.

Referring to FIG. 5 there is illustrated a cross-sectional view taken along lines 5—5 of FIG. 4, showing the sharp tips 26, 22 and 24 in position securing the skin surrounding the opening 30 with staple 34 fired in position. At this point in the closing sequence, the inward pressure on arms 12, 14 of the apparatus may be relieved to permit them to be opened by the resilient spring action and the sharp tips may be removed from the skin. Depending upon the nature and size of the opening in the skin, one or more of the staples may be fired in sequence and in adjacent end to end relation sufficient to maintain the opening in closed condition to promote healing. Thus, the nature of the staple and the capability of repeated firing will now be described.

The staple according to the invention is preferably constructed as a sharp tipped elongated member of naturally bioabsorbable material such as synthetic polymers or copolymers possessing a significant number of short-chain polyester linkages or other readily hydrolyzable linkages in their structure as, for example, is the case with polyglycolic acid, lactide-glycolide polymers, polydioxanone, polyalkylene glycols, polytrimethylene carbonate, polycaprolactone, their copolymers and related materials.

Preferably in the form of a rod as shown, the staple has a generally circular cross-section and must be of length at least sufficient to extend over at least two oppositely sloped surfaces of the skin on one side of the opening in order to prevent the staple from readily working its way out of the skin. To promote an even greater capability to maintain the portion of the staple in the skin, the staple preferably includes up to five or more slots 36 spaced along the length thereof to provide an irregular surface in engagement with the skin. This provides further stability to the staple and assists in preventing the staple from working its way out of the skin while retaining its rod-like configuration after application. The slots 36 may extend partially around the staple as shown in cross-section in FIG. 7, or they may be annular as to extend completely around the staple. It will be seen that in the preferred embodiment shown in the cross-section of FIG. 7, the slots 36 extend approximately between the 2 o'clock and 5 o'clock positions and the 7 o'clock and 10 o'clock positions. This feature is particularly significant in view of the undulating shape which the skin assumes at the interface between the two faces of the opening 30, which provides an environment for the rod to otherwise work itself out of the skin when the skin portions are shifted due to motions of the body.

The annular slots in the staple provide sufficient ridges and surface directional changes which engage the skin to prevent self working of the rod out of the skin. This feature is more clearly illustrated in FIG. 6 which shows the skin portions 28 surrounding the opening in cross-section and the staple 34 embedded therewithin. In one embodiment, the staple may be approximately 0.350 inch in length, have a major outer diameter between 0.015 and 0.016 inch and a minor dimension at the slots of between 0.012 and 0.013 inch. Preferably, the staple is of length at least equal to the dimension between the sharp skin engaging tips 22, 24 on extension 20. Clearly, however, the dimensions may be varied, depending upon the particular application contemplated.

Referring to FIG. 8 in conjunction with FIG. 1, one embodiment of a staple cartridge is illustrated which can provide repeated firing of staples subcuticularly into the skin as shown in FIG. 1. The apparatus includes a central arm 38 with staple cartridge 40 attached to the lower end. The cartridge contains a plurality of staples 34 in stacked relation as shown in FIG. 8, biased downwardly toward the firing chamber 42 by a plunger 44 and resilient spring arrangement 46 shown schematically in FIG. 8. Thus after each staple is fired, the staple next in line automatically positions itself in the chamber 42 under downward action of plunger 44. The cross-sectional dimension of chamber 42 is equal to or slightly greater than the major diameter of the staple 34 to facilitate a snug fit for the staple in the chamber.

The firing mechanism includes a staple firing plunger in the form of a flexible plunger wire 48 which is slidable through staple firing chamber 42 to engage the staple next in line to cause it to advance into the skin at a subcuticular level. The cross-section of firing wire 48 approximately matches the cross-section of staple 34 and is attached at the proximal end to rod 50 as shown in FIG. 1, which is slidable within opening 54 in guide housing 56 such that proximal upward movement of rod 50 causes withdrawal of wire 48, and distal downward movement thereof causes firing action by wire 48 on staple 34. Staple firing may be accomplished by manual downward distal movement of ring 58 attached to rod 50 as shown by set screw 52. Withdrawal of firing wire 48 out of firing chamber 42 is accomplished by manually moving ring 58 (and rod 52) proximally upwardly to permit the next staple 34 to enter the firing chamber 42 under downward action of spring 46. Further guidance for rod 50 is provided by proximally located second external guide housing 60 which contains a second guide opening 62 for reception of rod 50. Thus the two guide housings 56 and 60 serve to firmly position rod 50.

The firing movements of wire 48 may be adjusted by resetting the position of rod 50 relative to ring 58 by loosening set screw 52 and setting the desired position of rod 50. Further, it is noted that guide openings 54 and 62 are circular in cross-section almost equal to or slightly greater in dimension than rod 50. Sufficient clearance is provided to guide rod 50 yet to maintain steady slidable movement of the rod. Plunger wire 48 has a cross-sectional dimension slightly less than staple firing chamber 42 but sufficient to maintain steady distal and proximal movement therewithin while engaging the proximal end face of the staple. The staple 34 and the firing wire 48 are similarly dimensioned in cross-section such that engagement of the proximal surface of the staple by the wire 48 results in even and steady distal movement of the staple when the wire is advanced distally.

In operation, the apparatus is inserted into the opening in the skin closest to one end with the jaws 18, 20 positioned in respective engagement with the opposed marginal skin portions adjacent the opening. The jaws are advanced toward the skin sufficient to cause the sharp tips 26, 22 and 24 to grip the skin by piercing the outer layer or layers. Thereafter, the arms 12, 14 are manually drawn together to cause the skin to engage each other and to form an irregular, or undulating shape. At this time, the staple 34 is fired into the cutaneous matter as shown in FIG. 4 to retain the opposed skin portions together. The jaws are then withdrawn from the skin and the procedure is repeated in the area next adjacent the inserted fastener a sufficient number of times to close the entire opening in the skin.

Although a preferred embodiment of the multiple fire staple cartridge has been described, the structures and embodiments of alternative staple magazines may be utilized in combination with the multiple tip attachment feature which permit subcuticular stapling of an opening in body tissue. Further, although the preferred embodiment herein contemplates subcuticular attachment of cutaneous matter, it is well within the contemplated invention to apply such staples at subcutaneous levels, ie. below the epidermis and dermis. Such applications would involve minor variations of the dimensional relation between the sharp tips 22, 24 and 26 and the staple firing chamber 42.

It can be readily appreciated that a surgical opening or wound in the skin can be stapled utilizing the apparatus of the invention, leaving little or no extraneous staple markings or puncture wounds. Further, the resulting opening in the skin can be attached with greater precision and accuracy with the result that improved healing may be promoted with less visible wound indicia.

What is claimed is:

1. A surgical apparatus for attaching at least two adjacent opposed end portions of cutaneous body tissue, which comprises:
    a) a pair of opposed jaws movable toward and away from each other;
    b) body tissue engaging means extending from each jaw and facing the opposed jaw for engaging the respective opposed portions of the body tissue, such that when said jaws are moved toward each other said body tissue engaging means causes the two end portions of the body tissue to be displaced toward each other and engage at an engagement interface thereof so as to assume an irregular shape; and
    c) fastener storing means positioned proximal of said pair of opposed jaws for storing at least one generally elongated fastener, such fastener defining a generally longitudinal axis;
    d) means for advancing such at least one elongated fastener in generally the same direction as said longitudinal axis and generally medially of such body tissue engagement interface to thereby attach the opposed end portions of the body tissue.

2. The apparatus according to claim 1 wherein said storing means comprises a cartridge positioned adjacent said jaws and adapted to support a plurality of rod-like members.

3. An apparatus for attaching at least two adjacent end portions of cutaneous body tissue defining an opening which comprises:
    a) a pair of opposed jaws movable toward and away from each other;
    b) body tissue engaging means attached to each jaw and facing the opposed jaw, said body tissue engaging means on each said jaw being configured, dimensioned, and relatively positioned such that when said jaws are respectively positioned against the end portions of the body tissue and said jaws are moved toward each other, said body tissue engaging means engage the end portions of the body tissue adjacent the opening and cause them to engage each other and to assume an undulating shape at the interface thereof;

c) fastener storing means positioned proximal of said body tissue engaging means for storing at least one generally elongated attaching member; and d) means cooperative with said fastener storing means for directing such at least one elongated attaching member from a position generally medially and subcuticularly of the body tissue at such body tissue engagement interface to thereby attach the end portions.

4. The apparatus according to claim 3 wherein at least two elongated arms are connected to each other at one end portion and resiliently biased away from each other at the free end portion and said jaws are each respectively positioned at the free end portion of one of said arms.

5. The apparatus according to claim 4 wherein each jaw forms an obtuse angle with said respective elongated arm.

6. An apparatus for attaching at least two adjacent end portions of cutaneous body tissue defining an opening which comprises:

a) first and second opposed jaws adapted to be selectively moved toward and away from each other;

b) at least one generally pointed member extending away from said first jaw and generally toward said opposite jaw and at least two generally pointed members extending from said second jaw and generally toward said first jaw, whereby when said first and second jaws are respectively positioned against the end portions of the body tissue and said jaws are moved toward each other, said generally pointed members of said jaws engage the end portions of the body tissue adjacent the opening and cause them to engage each other and to assume an undulating shape at the interface thereof;

c) means positioned proximal of said jaws for storing at least one generally elongated body tissue attaching member; and d) means cooperative with said storing means for directing such at least one elongated body tissue attaching member generally medially and subcuticularly of the body tissue at such body tissue engagement interface to thereby attach the end portions.

7. The apparatus according to claim 6 wherein said two sharp pointed members are positioned in spaced relation on said second jaw and said first jaw includes said one sharp pointed member extending therefrom toward said second jaw at a location generally medially between said two sharp pointed members of said second jaw.

8. The apparatus according to claim 7 wherein said respective sharp pointed members are positioned for engagement with marginal end portions of the cutaneous body tissue adjacent an opening therein such that when said jaws are displaced toward each other, the body tissue portions move toward each other and into engagement and assume said undulating configuration at the interface therebetween.

9. The apparatus according to claim 8 wherein said storing means comprises a cartridge positioned adjacent said jaws and adapted to support a plurality of elongated body tissue attaching members.

10. The apparatus according to claim 9 wherein said cartridge includes means to resiliently bias said rod-like members toward a position for advancing the members distally toward the body tissue when the body tissue is gripped by said sharp pointed members.

11. The apparatus according to claim 9 wherein said body tissue attaching members are constructed of a bioabsorbable material.

12. The apparatus according to claim 11 wherein each body tissue attaching member is a rod-like member having a sharp pointed tip at the distal end to facilitate subcuticular penetration of the body tissue.

13. The apparatus according to claim 12 wherein each rod-like member includes at least one slot extending at least partially around a peripheral portion thereof.

14. The apparatus according to claim 13 wherein each said rod-like member includes a plurality of partially annular slots extending over surface portions thereof.

15. The apparatus according to claim 14 wherein said slots are five partially annular cut-out portions on opposed sides of each said rod-like member to provide a discontinuous surface to said rod-like member to retain said rod-like member in position within the body-tissue due to the interface between the body tissue and said discontinuous surface.

16. The apparatus according to claim 15 wherein said cartridge includes means to resiliently bias said rod-like members toward a position for advancing the member distally toward the body tissue when the body tissue is gripped by said sharp pointed members.

17. The apparatus according to claim 16 wherein said attaching member directing means is structured to individually advance each rod-like member subcuticularly into the body tissue for attachment of the two end portions thereof while the end portions are retained in engaged relation by said sharp pointed members.

18. The apparatus according to claim 17 wherein said attaching member directing means is an elongated flexible member of approximately the same cross-sectional dimension and shape as said rod-like member and positioned to engage one end portion of said rod-like member to cause distal movement thereof into the body tissue.

19. The apparatus according to claim 18 further comprising rigid means attached to said flexible member to assist selective movement of said flexible member in distal and proximal directions.

20. The apparatus according to claim 19 further comprising means to guide said flexible member in distal and proximal directions respectively toward and away from said cartridge.

21. The apparatus according to claim 20 wherein said means attached to said flexible member is an elongated rigid rod positioned for guided movement toward and away from said cartridge and said rod-like members.

22. The apparatus according to claim 21 further comprising a handle attached to said rigid rod for manually moving said rigid rod and said elongated flexible member toward and away from said cartridge and said rod-like members.

23. The apparatus according to claim 22 wherein said flexible member is a wire-like member.

24. The apparatus according to claim 23 wherein said sharp pointed members and said rod-like members are respectively spaced to fire said rod-like member subcutaneously into the body tissue when the tissue is gripped by said sharp pointed members.

25. A surgical apparatus for subcutaneously attaching two adjacent end portions of skin defining an opening, which comprises:

a) a pair of elongated members connected at one end portion and having two opposed jaws respectively positioned at the free end portion, said members being resiliently biased away from each other and adapted to be moved toward and away from each other;

b) at least two generally sharp skin engaging members attached to a first of said jaws and extending in a direction generally toward the second of said jaws;

c) at least one generally sharp skin engaging member attached to said second jaw and extending in a direction generally toward the first jaw, said skin engaging members being relatively positioned such that when said jaws are opened and said members are positioned against the end portions of the skin adjacent an opening therein, and the jaws are moved toward each other with the two adjacent end portions of skin gripped therebetween, said generally sharp skin engaging members engage the marginal end portions of skin adjacent the opening and cause them to assume an undulating shape; and d) means movable toward said first and second jaws for advancing a fastener member into the body tissue.

26. The apparatus according to claim 25 wherein said two generally sharp skin engaging members are attached to said first jaw in spaced relation to each other and said one generally sharp skin engaging member attached to said second jaw is positioned generally medially of said skin engaging members on said first jaw.

27. A method of attaching two adjacent end portions of skin surrounding an opening, comprising:

a) displacing the two end portions of skin surrounding the opening toward each other in a manner to cause said portions to engage each other and to assume an irregular shape at the interface; and b) introducing an elongated fastener into the end portions of the skin substantially subcuticularly, said elongated fastener being of length and shape sufficient to penetrate at least two spaced portions of skin on the same side of the opening so as to retain the marginal end portions thereof together in end to end contacting relation to promote healing.

28. The method according to claim 27 wherein said step of displacing the two end portions of skin together comprises:

a) gripping one marginal end portion of the skin adjacent the opening at two locations; and b) gripping the opposite marginal end portions of the skin at a location generally medial of the two locations at which the first marginal portion is gripped.

29. The method according to claim 27 further comprising releasing the skin portions after introduction of said elongated staple and repeating said steps of displacing the end portions of skin toward each other and introducing said elongated staple into the end portions of skin subcuticularly.

30. The method according to claim 27 wherein said staple is inserted subcutaneously.

31. The method according to claim 30 further comprising configuring said staple to have an irregular outer surface to prevent said staple from working itself out of the subcuticular region.

32. A method of attaching two adjacent end portions of skin surrounding an opening, comprising:

a) gripping one marginal end portion of the skin adjacent the opening at two locations and gripping the opposite marginal end portion of the skin at a location generally medial of the two locations at which the first marginal portion is gripped;

b) displacing the two end portions of skin surrounding the opening toward each other such that said portions engage each other to assume an irregular shape at the interface;

c) individually introducing an elongated staple into the skin portions subcuticularly, said elongated staple being of length and shape sufficient to penetrate at least two spaced portions of skin on the same side of the open so as to retain the marginal end portions thereof together in end to end contacting relation to promote healing; and d) repeating steps (a–c) as desired so as to sequentially introduce individual staples into the skin portions subcuticularly.

33. The method according to claim 32 further comprising repeating steps a–c until the entire skin opening is maintained in a closed condition.

34. A surgical apparatus for engaging first and second body portions which comprises:

a) a pair of opposed jaws;

b) at least two spaced apart tissue engaging means positioned on a first of said jaws and adapted to engage the first body tissue portion;

c) at least one tissue engaging means positioned on a second of said jaws at a location generally between said first two tissue engaging means on said first jaw and adapted to engage the second body tissue portion, said jaws movable toward each other so as to approximate the first and second body tissue portions; and d) means movable toward said jaws for advancing fastener members generally between said jaws to attach the body tissue portions.

35. A surgical apparatus for engaging first and second spaced body tissue portions and advancing elongated fastener members, which comprises:

a) a pair of opposed jaws;

b) at least two spaced apart tissue engaging means positioned on a first of said jaws and adapted to engage one of the body tissue portions;

c) at least one tissue engaging means positioned on said second jaw, said last mentioned tissue engaging means positioned with respect to said first two tissue engaging means on said first jaw such that when said tissue engaging means are respectively positioned in engagement with the body tissue portions, and said jaws are advanced toward each other sufficient to cause the tissue portions to engage each other, the tissue portions assume an irregular shape at the interface thereof, said jaws movable toward each other so as to approximate said first and second body tissue portions; and d) means movable toward said jaws for individually advancing elongated fastener members generally medially of said jaws to attach the body tissue portions.

36. A surgical apparatus for engaging first and second spaced body tissue portions and advancing fastener members, which comprises:

a) a pair of opposed jaws;

b) at least two spaced apart tissue engaging members positioned on a first of said jaws and adapted to engage one of the body tissue portions;

c) at least one tissue engaging member positioned on said second jaw, said last mentioned tissue engaging member positioned with respect to said first two tissue engaging members on said first jaw such that when said tissue engaging members are respectively positioned in engagement with the body tissue portions, and said jaws are advanced toward each other sufficient to cause the tissue portions to engage each other, the tissue portions assume an irregular shape at the interface thereof;

d) means for supporting said jaws to facilitate movement toward each other so as to approximate said first and second body tissue portions; and e) means movable toward said jaws for individually advancing fastener members from a position proximal of said jaws to a position between said jaws.

37. A surgical apparatus for engaging first and second body tissue portions and advancing a fastener member, which comprises:

a) a pair of opposed jaws;

b) at least two tissue engaging members positioned in spaced relation on a first of said jaws and extending in a direction generally toward said second jaw;

c) at least one tissue engaging member positioned on a second of said jaws and extending generally in a direction toward said first jaw such that said tissue engaging members may be positioned in respective engagement with the body tissue portions and said jaws moved toward each other to move the correspondingly positioned body tissue portions toward each other therewith in engaged relation, said at least one tissue engaging member on said second jaw being positioned between said at least two tissue engaging members on said first jaw; and d) means positioned proximal of said jaws for advancing a fastener member into such engaged body tissue portions.

38. The apparatus according to claim 37 wherein such fastener member is elongated.

39. The apparatus according to claim 38 further comprising means to store a plurality of such elongated fastener members and said fastener member advancing means is adapted for individually advancing such fastener members.

40. A surgical apparatus for attaching at least two adjacent end portions of cutaneous body tissue, which comprises:

a) a pair of opposed jaws movable toward and away from each other;

b) means positioned proximal of said jaws for storing a plurality of skin attaching fasteners, said fasteners comprising a generally straight rod-like elongated member having a sharp pointed tip at the distal end to facilitate subcuticular penetration into the marginal end portions of cutaneous body tissue to retain the end portions together, said member having at least one at least partially annular slot extending over a peripheral portion thereof to prevent exit from the cutaneous body tissue; and c) body tissue engaging means extending from each jaw and facing the opposed jaw for engaging the respective opposed portions of the body tissue such that when the jaws are moved toward each other said engaging means causes the two end portions of the body tissue to be displaced toward each other and engage at the interface thereof so as to assume an irregular shape whereby said at least one elongated member may be directed generally medially of such body tissue engagement interface to thereby attach the opposed portions of the body tissue.

41. An apparatus for attaching at least two adjacent end portions of cutaneous body tissue defining an opening which comprises:

a) at least two elongated arms connected to each other at one end portion and resiliently biased away from each other at the free end portion;

b) a jaw positioned at the free end portion of each of said arms and movable toward and away from each other when said arms are moved toward and away from each other;

c) body tissue engaging means attached to each jaw and facing the opposed jaw, and being configured and dimensioned such that when said jaws are respectively positioned against the end portions of the body tissue and said jaws are moved toward each other, said body tissue engaging means engage the end portions of the body tissue adjacent the opening and cause them to engage each other and to assume an undulating shape at the interface thereof; and d) means movable toward said jaws to introduce and direct an elongated attaching member generally medially and subcuticularly of the body tissue at the interface to thereby attach the end portions.

42. A surgical fastening apparatus which comprises:

a) a pair of jaws, each of said jaws having means for gripping a body tissue portion, said jaws movable toward each other to move the body tissue portions toward each other;

b) fastener storing means positioned adjacent said pair of jaws and storing at least one elongated fastener; and c) means cooperative with said fastener storing means for introducing and directing said at least one elongated fastener into the body tissue portions at a location such that contact between said fastener and said jaws is avoided.

43. The surgical fastening apparatus according to claim 42 wherein said pair of jaws are normally biased away from each other.

44. The surgical fastening apparatus according to claim 42 wherein said gripping means comprises at least one sharp pointed member extending from each of said jaws.

45. The surgical fastening apparatus according to claim 42 wherein said fastener directing means comprises a member having a distal surface adapted to contact a proximal surface of said at least one fastener.

46. The surgical fastening apparatus according to claim 45 wherein said fastener storing means is configured to store a plurality of fasteners in stacked relation.

47. The surgical fastening apparatus according to claim 42 wherein said at least one fastener is composed of a bioabsorbable material.

48. A surgical fastening apparatus which comprises:

a) a pair of jaws, each of said jaws having means for gripping a body tissue portion, said jaws being supported by support means and movable toward each other to move the body tissue portions toward each other into engagement;

b) means positioned adjacent said jaws for storing a plurality of elongated rod-like fasteners in generally vertically stacked relation; and c) means cooperative with said fastener storing means for contacting and directing a bottommost fastener of said plurality of stacked fasteners into such engaged body tissue portions.

49. A surgical fastening apparatus which comprises:
a) a first tissue gripping member;
b) a second tissue gripping member;
c) means for moving at least one of said tissue gripping members towards said other tissue gripping member;
d) fastener storing means positioned proximal of said tissue gripping members and storing at least one elongated fastener, said elongated fastener defining a generally longitudinal axis; and
e) means for advancing said at least one elongated fastener into the tissue in generally the same direction as said longitudinal axis after at least one of said tissue gripping members is moved towards the other member.

50. The surgical fastening apparatus according to claim 49 wherein said first and second gripping members each comprise at least one sharp pointed member.

51. The surgical fastening apparatus according to claim 50 wherein said at least one sharp pointed member on said first and second gripping members extends inwardly.

52. The surgical fastening apparatus according to claim 49 wherein said elongated fastener has a pointed tip.

53. The surgical fastening apparatus according to claim 49 wherein said fastener storing means comprises a cartridge for supporting a plurality of elongated fasteners in stacked relation.

54. The surgical fastening apparatus according to claim 49 wherein said fastener directing means is adapted to come into contact with a proximal end of said fastener to direct it subcuticularly into the tissue.

55. The surgical fastening apparatus according to claim 49 further comprising means for biasing said first and second gripping members away from each other.

56. The surgical fastening apparatus according to claim 49 wherein said at least one fastener is composed of a bioabsorbable material.

57. An apparatus for attaching at least two adjacent end portions of cutaneous body tissue defining an opening which comprises:
a) first and second elongated arms connected to each other at one end portion and adapted to be selectively moved toward and away from each other, said elongated arms resiliently biased away from each other at the free end portions thereof;
b) first and second opposed jaws respectively positioned at the free end portions of said first and second elongated arms, and forming an obtuse angle with said respective elongated arm, said first jaw including at least one sharp pointed member extending away from said jaw and generally toward said opposite jaw, said second jaw including at least two sharp pointed members extending therefrom and generally toward said first jaw, whereby when said first and second jaws are respectively positioned against the end portions of the body tissue and said jaws are moved toward each other, said pointed members of said jaws engage the end portions of the body tissue adjacent the opening and cause them to engage each other and to assume an undulating shape at the interface thereof;
c) means spaced from said jaws for storing at least one generally elongated attaching member; and
d) means adapted to cooperate with said storing means for directing said at least one elongated attaching member generally medially and subcuticularly of the body tissue at such body tissue engagement interface to thereby attach the end portions.

58. A surgical apparatus for attaching at least two adjacent end portions of cutaneous body tissue, which comprises:
a) a pair of opposed jaws;
b) means for supporting said jaws for movement toward and away from each other;
c) means spaced from said pair of opposed jaws for storing at least one generally elongated fastener member;
d) body tissue engaging means extending from each jaw and facing the opposed jaw for engaging the respective opposed portions of the body tissue, one of said jaws having a greater number of body tissue engaging means than said other jaw, said body tissue engaging means being respectively configured, dimensioned and relatively positioned such that when said jaws are moved toward each other said body tissue engaging means causes the two end portions of the body tissue to be displaced toward each other and engage at the interface thereof so as to assume an irregular shape; and
e) means movable for engagement with such elongated fastener member for directing such at least one elongated member generally medially of such body tissue engagement interface to thereby attach the opposed portions of the body tissue.

59. A surgical apparatus for attaching at least two end portions of cutaneous body tissue adjacent an opening in the body tissue, which comprises:
a) first tissue gripping member;
b) second tissue gripping member positioned opposite and movable toward said first tissue gripping member;
c) at least one elongated tissue fastening member supported proximal of said tissue gripping members; and
d) a pusher engagable with said at least one elongated tissue fastening member for advancing said at least one elongated tissue fastening member into the body tissue without substantial deformation by said tissue fastening member.

60. A surgical apparatus for attaching at least two end portions of cutaneous body tissue adjacent an opening in the body tissue, which comprises:
a) first tissue gripping member;
b) second tissue gripping member movable toward said first tissue gripping member such that engagement of said first and second tissue gripping members with the respective end portions of cutaneous body tissue and movement of said first and second tissue gripping members toward each other causes the end portions to move toward each other to form an irregular surface at the interface thereof;
c) at least one elongated fastener member supported proximally of said gripping members; and
d) a pusher proximal of said tissue gripping members and engagable with said at least one elongated fastener member for advancement of an elongated fastening member longitudinally with respect to the opening in the body tissue.

* * * * *